US010059964B2

(12) United States Patent
Masuda et al.

(10) Patent No.: US 10,059,964 B2
(45) Date of Patent: Aug. 28, 2018

(54) SUCROSE UNASSIMILATING FLOCCULENT YEAST

(71) Applicant: ASAHI GROUP HOLDINGS, LTD., Tokyo (JP)

(72) Inventors: Takayuki Masuda, Abiko (JP); Taku Kato, Takasago (JP)

(73) Assignee: ASAHI GROUP HOLDINGS, LTD., Tokyo (JP)

( * ) Notice: Subject to any disclaimer, the term of this patent is extended or adjusted under 35 U.S.C. 154(b) by 57 days.

(21) Appl. No.: 14/888,603

(22) PCT Filed: Apr. 30, 2014

(86) PCT No.: PCT/JP2014/062415
§ 371 (c)(1),
(2) Date: Nov. 2, 2015

(87) PCT Pub. No.: WO2014/181848
PCT Pub. Date: Nov. 13, 2014

(65) Prior Publication Data
US 2016/0108438 A1    Apr. 21, 2016

(30) Foreign Application Priority Data
May 9, 2013  (JP) ................................. 2013-099537

(51) Int. Cl.
| *C12N 1/18* | (2006.01) |
| *C12P 7/06* | (2006.01) |
| *C12R 1/865* | (2006.01) |
| *C12P 19/14* | (2006.01) |
| *C12N 3/00* | (2006.01) |
| *C13B 30/06* | (2011.01) |

(52) U.S. Cl.
CPC ................. *C12P 7/06* (2013.01); *C12N 1/18* (2013.01); *C12N 3/00* (2013.01); *C12P 19/14* (2013.01); *C12R 1/865* (2013.01); *C13B 30/06* (2013.01); *Y02E 50/17* (2013.01)

(58) Field of Classification Search
None
See application file for complete search history.

(56) References Cited

U.S. PATENT DOCUMENTS 4,335,207 A * 6/1982 Heady ................. C08B 37/0051
435/101
2011/0200710 A1    8/2011 Ohara et al.

FOREIGN PATENT DOCUMENTS

| CN | 102159721 A | 8/2011 |
| EP | 2 339 012 A1 | 6/2011 |
| EP | 2896699 A1 | 7/2015 |
| JP | 5-236942 A | 9/1993 |
| RU | 2383614 C1 | 3/2010 |
| WO | 2010/032724 A1 | 3/2010 |
| WO | 2014042184 A1 | 3/2014 |

OTHER PUBLICATIONS

Gascon et al., J. Biol. Chem. 1968, 243:1573-1577.*
International Preliminary Report on Patentability and Written Opinion dated Nov. 19, 2015 from the International Searching Authority in counterpart International Application No. PCT/JP2014/062415.
V. Birckner, et al., "Invertase-Free Yeasts and Their Application in the Selective Fermentation of Final Cane Molasses as a Preliminary Step to Desugarization", Industrial and Engineering Chemistry, Mar. 1928, pp. 267-275, vol. 20, No. 3.
Database WPI, Week 201424, Thomson Scientific, AN 2014-F13579, XP002727413, London, GB, 4 pages (2014).
Frederique Bidard, et al., "The *Saccharomyces cerevisiae* FLO1 Flocculation Gene Encodes for a Cell Surface Protein", Yeast, 1995, pp. 809-822, vol. 11.
Osamu Kobayashi, et al., "Region of Flo1 Proteins Responsible for Sugar Recognition", Journal of Bacteriology, Dec. 1988, pp. 6503-6510, vol. 180, No. 24.
Takashi Shinohara, et al., "Introduction of Flocculation Property into Wine Yeasts (*Saccharomyces cerevisiae*) by Hybridization", Journal of Fermentation and Bioengineering, 1997, pp. 96-101, vol. 83, No. 1.
Junji Watari, et al., "Construction of Flocculent Yeast Cells (*Saccharomyces cerevisiae*) by Mating or Protoplast Fusion Using a Yeast Cell Containing the Flocculation Gene FLO5", Agric. Biol. Chem., 1990, pp. 1677-1681, vol. 54, No. 7.
JPO Office Action for Application No. 2013-099537 dated Sep. 24, 2014.
International Search Report for PCT/JP2014/062415 dated Jul. 31, 2014 [PCT/ISA/210].
Written Opinion for PCT/JP2014/062415 dated Jul. 31, 2014 [PCT/ISA/237].
Sieiro, C., et al., "Flocculation of industrial and laboratory strains of *Saccharomyces cerevisiae*", Journal of Industrial Microbiology, 1995, vol. 14, pp. 461-466 (6 pages total).
Communication dated Dec. 18, 2017 from the Russian Patent Office in counterpart Russian application No. 2015146615/10.
Carlson, M., et al., "Mutants of Yeast Defective in Sucrose Utilization", Genetics, 98 (1), May 1981, pp. 25-40 (16 pages).

* cited by examiner

*Primary Examiner* — Irene Marx
(74) *Attorney, Agent, or Firm* — Sughrue Mion, PLLC

(57) ABSTRACT

An object of the present invention is to provide a sucrose unassimilating yeast which has a flocculation ability and has much of a proven performance of food production. The present invention pertains to a yeast strain expressed by accession number: NITE BP-1587.

5 Claims, 7 Drawing Sheets

Fig. 4A
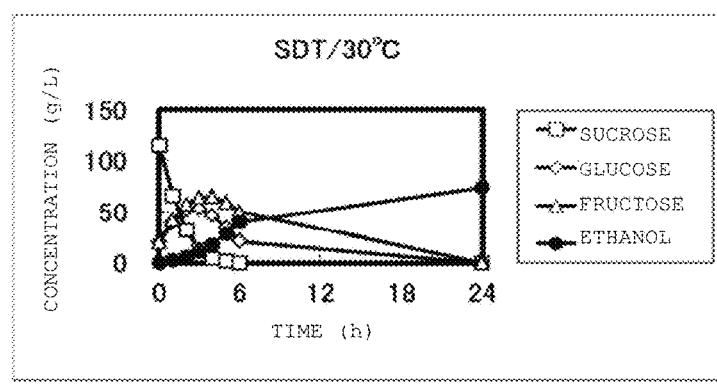
Fig. 4B
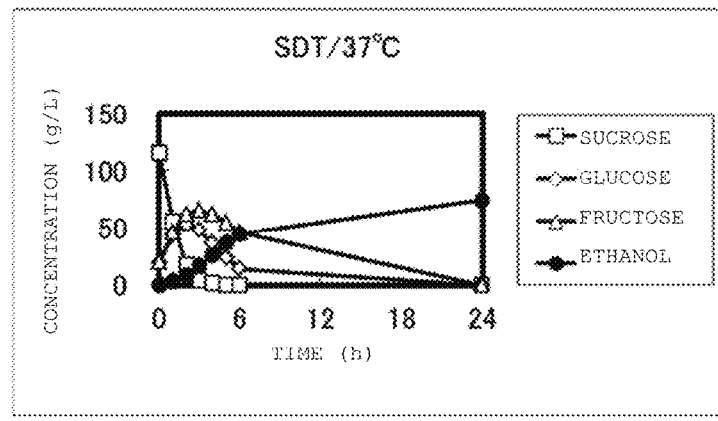
[Fig. 5]
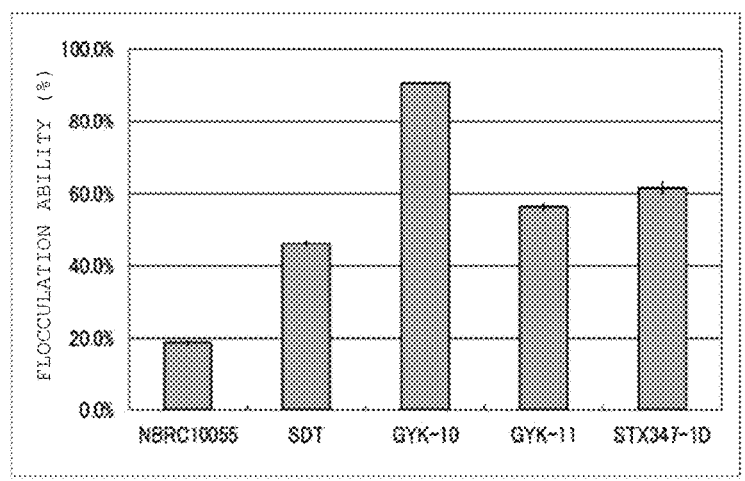

SUCROSE UNASSIMILATING FLOCCULENT YEAST

CROSS REFERENCE TO RELATED APPLICATIONS

This application is a National Stage of International Application No. PCT/JP2014/062415, filed on Apr. 30, 2014, which claims priority from Japanese Patent Application No. 2013-099537, filed on May 9, 2013, the contents of all of which are incorporated herein by reference in their entirety.

TECHNICAL FIELD

The present invention relates to a sucrose unassimilating yeast, and especially relates to a sucrose unassimilating yeast belonging to Saccharomyces cerevisiae.

BACKGROUND ART

Ethanol for fuel derived from a plant is expected to be a liquid fuel alternative to gasoline to prevent increase in carbon dioxide gas, and a method for producing ethanol by fermenting sugar liquid derived from a plant with microorganisms has been conventionally investigated. However, there is a problem that consumption of sugar liquid derived from a plant as a raw material for production of ethanol puts pressure on production of sugar, which is food.

As a method for solving this problem, Patent Document describes a method for producing sugar and ethanol wherein a plant-origin sugar solution is fermented by a sucrose unassimilating yeast. According to this method, selective ethanol fermentation of reducing sugar is carried out using a sucrose unassimilating yeast before a sugar crystallization step. By means of this process, improvement in productivity of sugar and ethanol production are simultaneously achieved.

However, there has been conventionally almost no example of that a sucrose unassimilating yeast is utilized in food production, and there are few microbial species of which safety for a human body has been confirmed. Hence a method for producing sugar and ethanol using a sucrose unassimilating yeast has a problem that there are few microbial species which can be used therefor and that room for improvement in the process is limited.

Some sucrose unassimilating yeasts belong to Saccharomyces cerevisiae. Saccharomyces cerevisiae is a yeast strain which has much of a proven performance of food production, and excellent in safety for a human body. However, among the sucrose unassimilating yeasts belonging to Saccharomyces cerevisiae, a yeast which is excellent in fermentability is non-flocculent and hardly sediments. Therefore, troublesome operations such as centrifugation and microfiltration are required for removing the yeast from a sugar liquid after fermentation.

Here, among the sucrose unassimilating yeasts belonging to Saccharomyces cerevisiae, a yeast which exhibits flocculation (STX 347-1D strain) is auxotrophic, and has a problem that fermentation hardly progresses in a case where uracil (a base) and histidine (an amino acid) are not present in a medium.

Therefore, as for a method for producing sugar and ethanol using a sucrose unassimilating yeast, it is still difficult to expand the production scale and reduce production cost, while securing production conditions excellent in safety and practicality.

PRIOR ART DOCUMENT

Patent Document

[Patent Document 1] Japanese Patent No. 4883511

SUMMARY OF THE INVENTION

Problems to be Solved by the Invention

The present invention solves the above-mentioned conventional problems, and an object thereof is to provide a sucrose unassimilating yeast which has a flocculation ability and has much of a proven performance of food production.

Means for Solving the Problems

The present invention provides a yeast strain expressed by accession number: NITE BP-1587.

In addition, the present invention provides a yeast strain expressed by accession number: NITE BP-1588.

In addition, the present invention provides a method for producing sugar and ethanol using either of the above-mentioned yeast strains.

Effects of the Invention

The yeast strain expressed by accession number: NITE BP-1587 is sucrose unassimilating, and exhibits high flocculation ability. In addition, this yeast strain is also excellent in heat tolerance and acid tolerance. Furthermore, this yeast strain belongs to Saccharomyces cerevisiae, which has much of a proven performance of food production, and is safe for a human body.

BRIEF DESCRIPTION OF THE DRAWINGS

FIGS. 4A and 4B are graphs showing how concentrations of saccharides and ethanol in sugar liquid change in a case where a sugar liquid is fermented using a flocculent yeast, which is a parent strain of the sucrose unassimilating flocculent yeast of the present invention.

FIG. 5 is graph of comparison of flocculation abilities of various yeasts.

MODE FOR CARRYING OUT THE INVENTION

Figure 1A:
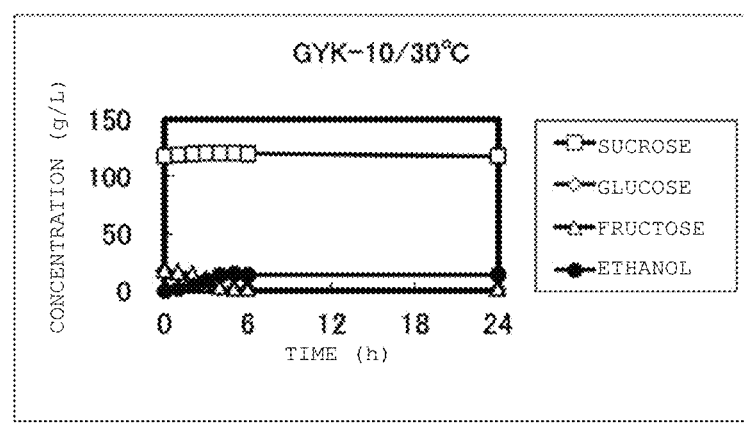
FIGS. 1A and 1B are graphs showing how concentrations of saccharides and ethanol in sugar liquid change in a case where a sugar liquid is fermented using a sucrose unassimilating flocculent yeast of the present invention (haploid).
Figure 1B:
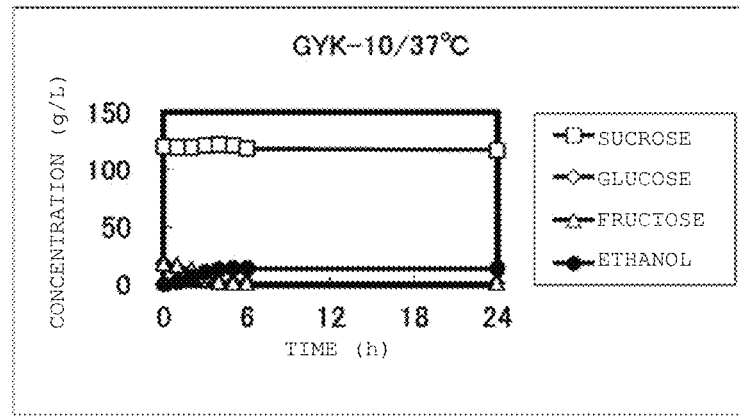
Figure 2A:
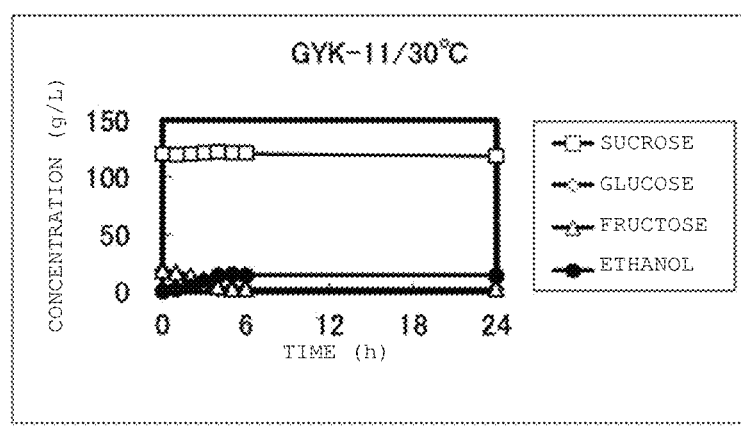
FIGS. 2A and 2B are graphs showing how concentrations of saccharides and ethanol in sugar liquid change in a case where a sugar liquid is fermented using a sucrose unassimilating flocculent yeast of the present invention (diploid).
Figure 2B:
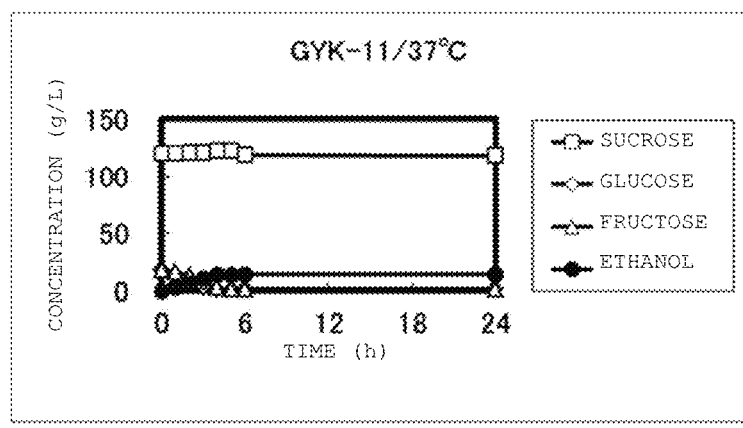
Figure 3A:
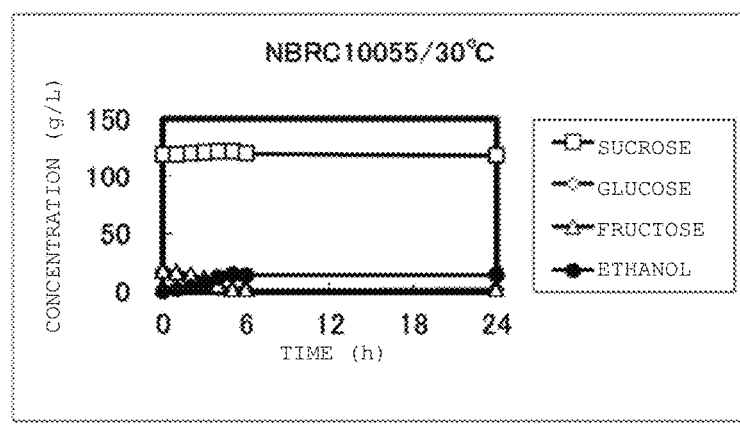
FIGS. 3A and 3B are graphs showing how concentrations of saccharides and ethanol in sugar liquid change in a case where a sugar liquid is fermented using a sucrose unassimilating yeast, which is a parent strain of the sucrose unassimilating flocculent yeast of the present invention.
Figure 3B:
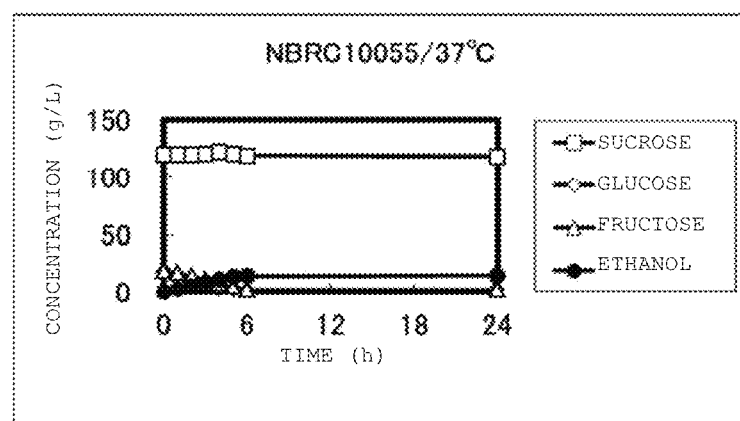

As a sucrose unassimilating yeast, *Saccharomyces cerevisiae* NBRC 10055 strain was prepared. NBRC 10055 strain was purchased from NBRC. NBRC 10055 strain is a *Saccharomyces* yeast isolated from red wine from Garcia (Spain). When this yeast was isolated, it was found that this yeast has a property of forming membrane after fermentation, a property of mainly fermenting glucose, a property of producing acetic acid under an aerobic condition, and the like.

In addition, as a flocculent yeast, *Saccharomyces cerevisiae* SDT strain was prepared. SDT strain is a strain found by the applicant, and confirmed to belong to *Saccharomyces cerevisiae*. SDT strain is deposited at NITE. Accession number of SDT strain is NITE BP-1589.

NBRC 10055 strain and SDT strain were independently subjected to spore isolation, to acquire an isolated spore showing type a or type α as a mating type. The isolated spore of NBRC 10055 and the isolated spore of NITE BP-1589 which have different mating types were mated using a manipulator, to create a mated strain. As for the created mated strain, tetrad dissection was carried out using a manipulator after induction of spore formation, to acquire an isolated spore. Next, MAT locus of the mated strain and the isolated spore was amplified by PCR method to carry out analysis, and the mating type was determined.

Screening was carried out on the obtained isolated spore, and a strain having an objective character of a sucrose unassimilating property and flocculation was selected, to acquire a sucrose unassimilating flocculent yeast of the present invention. This yeast strain is a haploid. The yeast was named GYK-10. The obtained strain was obtained from parent strains, both of which are *Saccharomyces cerevisiae*, and belongs to *Saccharomyces cerevisiae*. GYK-10 is deposited at NITE. Accession number of GYK-10 is NITE BP-1587.

GYK-10 was cultured on a YPD agar medium, and a diploidized yeast on the basis of a property of homothallism was selected. The yeast was named GYK-11. GYK-11 is deposited at NITE. Accession number of GYK-11 is NITE BP-1588.

A sucrose unassimilating property, a flocculent ability, heat tolerance and acid tolerance of GYK-10 and GYK-11 were tested as follows.

Test of Sucrose Unassimilating Property

As a test object yeast, GYK-10 and GYK-11, and NBRC 10055 and SDT, which are the parent strains thereof, were prepared.

A yeast cultured at 30° C. using 100 ml of a YPD liquid medium (1% yeast extract, 2% peptone, 2% glucose) was recovered by centrifugation (5,000×g, 5 minutes). The recovered yeast (wet weight: 1 g) was added to 100 ml of a sugar liquid prepared simulating sugar cane squeezed juice (1% yeast extract, 2% peptone, 12% sucrose, 1.5% glucose, 1.5% fructose), and the mixture was fermented at 30° C. or 37° C. As for concentrations of saccharides and ethanol contained in the sugar liquid, change with time during fermentation time was recorded. The results are shown in FIG. 1A to FIG. 4B.

According to the test results, it was confirmed that GYK-10 and GYK-11 are sucrose unassimilating, as with NBRC 10055, which is a parent strain.

Test of Flocculation Ability

As a test object yeast, GYK-10 and GYK-11, NBRC 10055 and SDT, which are the parent strains thereof, and *Saccharomyces cerevisiae* STX 347-1D strain, which is recognized to have a high flocculation ability, were prepared.

After the yeast cell was precultured in 5 mL of a YPD liquid medium (30° C., 48 hours, 120 rpm), the yeast cell was washed twice with twenty times the amount of distilled water to the volume of the cell. The washed cell was suspended in 4 mL of distilled water so that the concentration of wet cells was 20. After 250 μL of distilled water was added to 1 mL of the suspension liquid of cells, absorbance at 600 nm was determined (a control). Next, after 250 μL of 100 mM calcium chloride was added to 1 mL of the suspension liquid of cells, the mixture was settled for 5 minutes. Thereafter, absorbance at 600 nm was determined (a sample). Absorbance was determined using "spectrophotometer UV-1700" (manufactured by SHIMADZU CORPORATION).

The flocculation ability was determined according to the formula:

$$C=(1-B/A)\times 100$$

wherein C is a flocculation ability (%); A is absorbance of the control; and B is absorbance of the sample. The results are shown in Table 1 and FIG. 5.

TABLE 1

| ABSORBANCE | STRAIN | | | | |
|---|---|---|---|---|---|
| (600 nm) | NBRC10055 | SDT | GYK-10 | GYK-11 | STX347-1D |
| CONTROL (1) | 1.707 | 1.931 | 1.691 | 1.856 | 1.579 |
| CONTROL (2) | 1.694 | 1.913 | 1.704 | 1.845 | 1.608 |
| CONTROL (3) | 1.699 | 1.904 | 1.699 | 1.810 | 1.614 |
| SAMPLE (1) | 1.377 | 1.050 | 0.162 | 0.813 | 0.600 |
| SAMPLE (2) | 1.390 | 1.045 | 0.167 | 0.786 | 0.648 |
| SAMPLE (3) | 1.380 | 1.007 | 0.154 | 0.807 | 0.599 |
| FLOCCULATION ABILITY (1) (%) | 19.3% | 45.6% | 90.4% | 56.2% | 62.0% |
| FLOCCULATION ABILITY (2) (%) | 17.9% | 45.4% | 90.2% | 57.4% | 59.7% |
| FLOCCULATION ABILITY (3) (%) | 18.8% | 47.1% | 90.9% | 55.4% | 62.9% |
| FLOCCULATION ABILITY (AVERAGE) | 18.7% | 46.0% | 90.5% | 56.3% | 61.5% |

TABLE 1-continued

| ABSORBANCE | STRAIN | | | | |
|---|---|---|---|---|---|
| (600 nm) | NBRC10055 | SDT | GYK-10 | GYK-11 | STX347-1D |
| FLOCCULATION ABILITY (STANDARD DEVIATION) | 0.7% | 0.9% | 0.4% | 1.0% | 1.6% |

According to the test results, it was confirmed that the flocculent ability of GYK-10 is about twice higher as compared with that of SDT, which is a parent strain thereof, and about 1.5 times higher as compared with that of a general flocculent yeast STX 347-1D.

Test of Heat Tolerance and Acid Tolerance

As a test object yeast, GYK-10 and GYK-11, and NBRC 10055 and SDT, which are the parent strains thereof, were prepared.

After the yeast cell was precultured in 1 mL of a YPD liquid medium (30° C., one night, 120 rpm), the yeast cell was washed twice with 1 mL of sterilized water. The washed cell was added to a YPD liquid medium so that the concentration was $1 \times 10^6$ cells/mL. One hundred microliters of the suspension liquid of cells in YPD was added to well of a microtiter plate and underwent main culture, and absorbance at 600 nm was determined every 10 minutes. Absorbance at 600 nm was determined using "PLATE READER HiTS-S2" (manufactured by SCINICS CORPORATION).

Figure 6A:
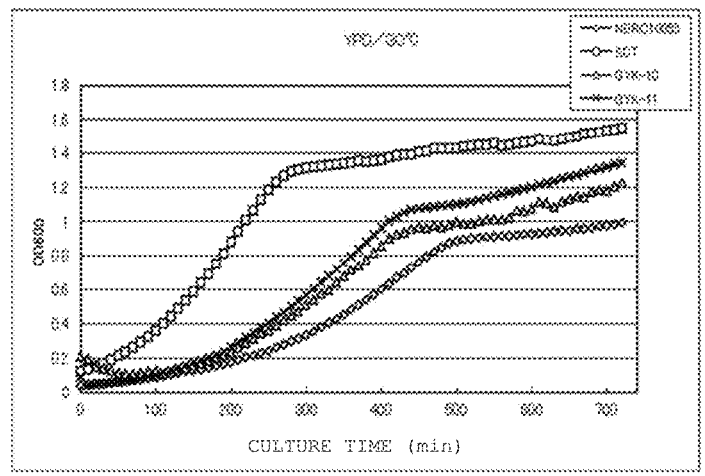
FIGS. 6A, 6B and 6C are graphs showing how the sucrose unassimilating flocculent yeast of the present invention and the parent strains proliferate in a case where the yeasts are cultured in a medium of which temperature is adjusted to 30° C., 37° C. or 40° C.
Figure 6B:
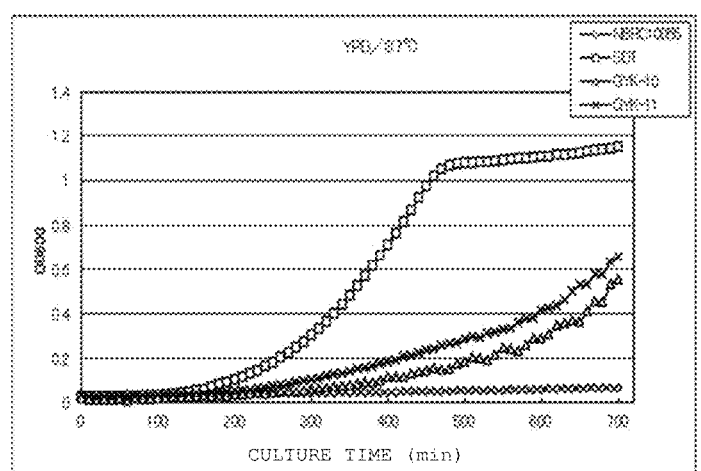
Figure 6C:
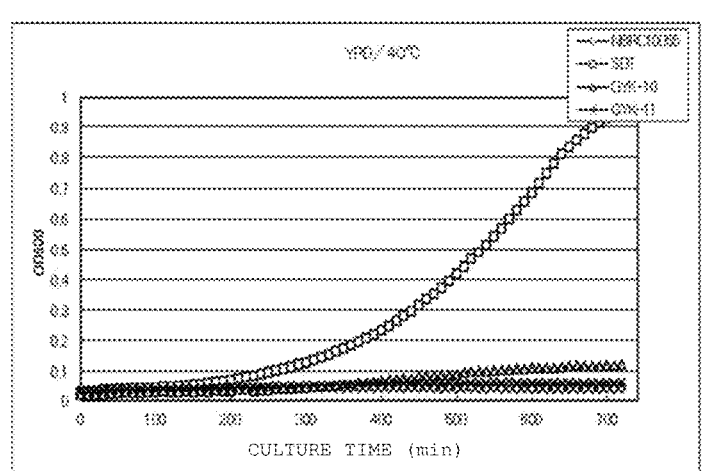

At that time, as a test of heat tolerance of the yeast, the suspension liquid of cells in YPD was cultured with adjusting the temperature to 30° C., 37° C. or 40° C. The results are shown in FIGS. 6A, 6B and 6C.

Heat tolerance of GYK-10 and GYK-11 is weaker than that of SDT, which is a parent strain, but stronger than that of NERC 10055. GYK-10 and GYK-11 do not have clear difference in heat tolerance.

Figure 7A:
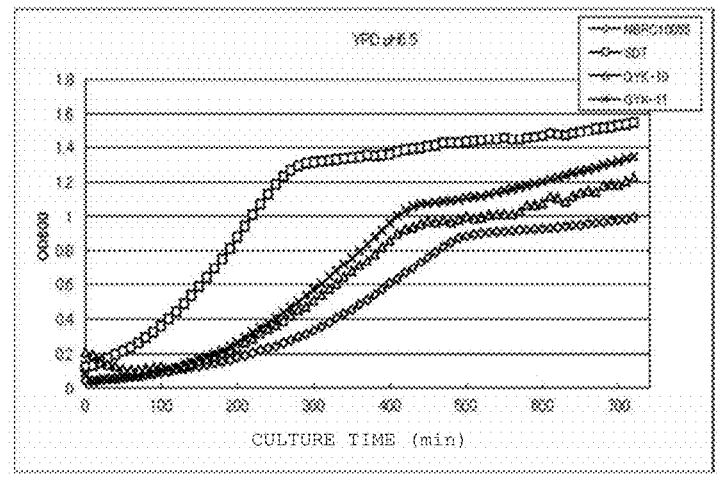
FIGS. 7A, 7B and 7C are graphs showing how the sucrose unassimilating flocculent yeast of the present invention and the parent strains proliferate in a case where the yeasts are cultured in a medium adjusted to pH 6.5, pH 3.0 or pH 2.0.
Figure 7B:
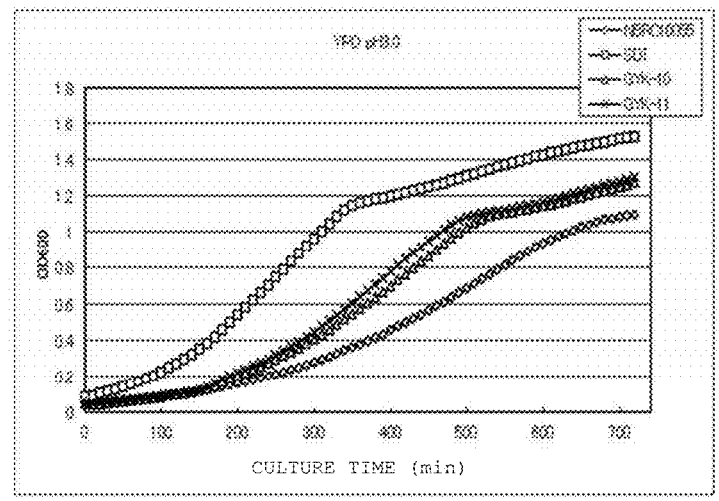
Figure 7C:
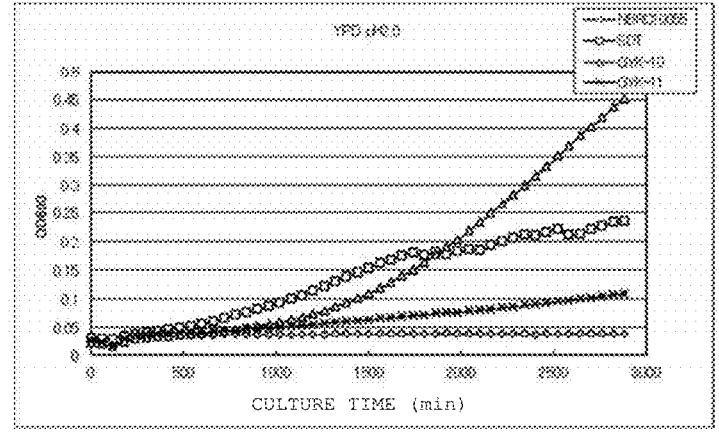

In addition, as a test of acid tolerance of the yeast, the yeast was cultured at 30° C. using a YPD (pH 6.5), YPD (pH 2.0), or YPD (pH 3.0) liquid medium. The results are shown in FIGS. 7A, 7B and 7C.

GYK-10 and GYK-11 are capable of growing in YPD of which pH is 2.0, and have acid tolerance stronger than that of SDT and NBRC 10055, which are the parent strains.

Method for Producing Sucrose and Ethanol

The sucrose unassimilating flocculent yeast of the present invention can be used for, for example, a method for producing sucrose and ethanol described in Patent Document 1. That is to say, first, sugar liquid derived from a plant is fermented using the sucrose unassimilating flocculent yeast of the present invention. The plant to be used at a raw material of the sugar liquid may be a plant which can accumulate sugar components, and examples thereof generally include sugar cane, sugar beet and the like. The sugar liquid may be a squeezed juice, a broth and the like of these plants. Next, the sucrose unassimilating flocculent yeast of the present invention is added to the sugar liquid, and ethanol fermentation is carried out at a given temperature under an anaerobic condition for an appropriate length of time.

As the sucrose unassimilating flocculent yeast of the present invention to be used for carrying out ethanol fermentation of the sugar liquid, either of GYK-10 or GYK-11 may be used. In addition, both can be concomitantly used. In a preferable embodiment, GYK-10 is used. GYK-10 is excellent in a flocculation property, and the yeast can be easily removed from sugar liquid after ethanol fermentation.

The sucrose unassimilating flocculent yeast of the present invention is excellent in heat tolerance, and fermentation can progress so long as the temperature is up to about 37° C. Preferable temperature for carrying out ethanol fermentation is 35° C. or higher at which cost of a cooling installation can be reduced, and the sucrose unassimilating yeast of the present invention can carry out fermentation in a low-cost installation.

The sugar liquid may be clarified by removing non-sugar components contained in the sugar liquid before carrying out ethanol fermentation. By such an operation, impurities contained in the sugar liquid are reduced, and it becomes easy to repeatedly utilize the yeast. The sucrose unassimilating flocculent yeast of the present invention has a flocculation ability, and an efficient method for fermentation wherein a flocculent yeast is always present in a fermenter and fermentation is continuously carried out without separation of yeasts becomes possible.

The fermented liquid obtained as a result of fermentation contains yeasts, ethanol, water, sucrose, minerals, amino acids and the like. Next, the fermented liquid is concentrated, and ethanol is recovered from the fermented liquid.

The recovery of ethanol from the fermented liquid can be carried out by a method known to one skilled in the art, and the method is, for example, separation of ethanol by distillation. When ethanol separation by distillation is carried out, the sugar liquid is concentrated at the same time. Thus, it is unnecessary to carry out heat concentration once again in production of sugar, and both time and energy can be saved.

The production of sugar from the fermented liquid can be carried out by a method known to one skilled in the art, and the method is, for example, crystallization of sugar, or the like. Specifically, the fermented sugar liquid is repeatedly subjected to heat concentration under vacuum suction in small portions (0.5 to 1 kl) to extract sugar crystal having a predetermined size or larger, and the concentrate is then separated into sugar crystal and sugar liquid with a centrifugal machine.

The sugar liquid separated from the sugar crystal is generally referred to as molasses. The molasses may be mixed with the cleaned liquid in an appropriate amount, to be used again as a fermentation raw material. Thus, the utilization efficiency of the sugar components contained in the sugar liquid is further improved.

Examples

The present invention is explained more specifically by means of the examples described below, but the present invention is not limited thereto.

1) Fermentation Test

After the yeast cell (GYK-10) was precultured in 5 L of a YPD liquid medium (1 L×5, 30° C., one night, 100 rpm), main culture was carried out in 100 L of a medium of 4% glucose and 3% yeast extract (100 L, 30° C., one night, stirring with aeration). After completion of culture, stirring with aeration was stopped, and 5.5 kg of flocculated and sedimented yeast was recovered.

After a medium simulating squeezed juice of sugar cane (Brix 15%, sucrose 9.9%, glucose 2.7%, fructose 2.8%), of which raw materials are brown sugar, glucose and fructose, was prepared, 5.5 kg of the yeast was added thereto, and fermentation was carried out (30° C., 4 hours). After completion of fermentation, stirring was stopped, and the yeast was flocculated and sedimented. Thereafter, the upper fermented liquid was recovered, and a small amount of left yeast was removed by a centrifugal machine, to give a clear liquid.

Concentrations of sucrose, glucose and fructose in the clarified fermented liquid were determined by liquid chromatography. SCR-101N (manufactured by SHIMADZU CORPORATION) was used as the column, and water was used as the mobile phase. Temperature of the column oven was set to 60° C. The results are shown in Table 2.

TABLE 2

|  | SUCROSE | GLUCOSE | FRUCTOSE |
| --- | --- | --- | --- |
| BEFORE FERMENTATION | 98.6 g/L | 27.4 g/L | 28.1 g/L |
| AFTER FERMENTATION | 98.6 g/L | 0.2 g/L | 0.0 g/L |

As shown in the fermentation test, GYK-10 is flocculated in the course of fermentation of the sugar liquid, and sedimented. In addition, GYK-10 did not assimilate sucrose, but selectively assimilated reducing sugar.

2) Test of Sugar Production

Figure 8:
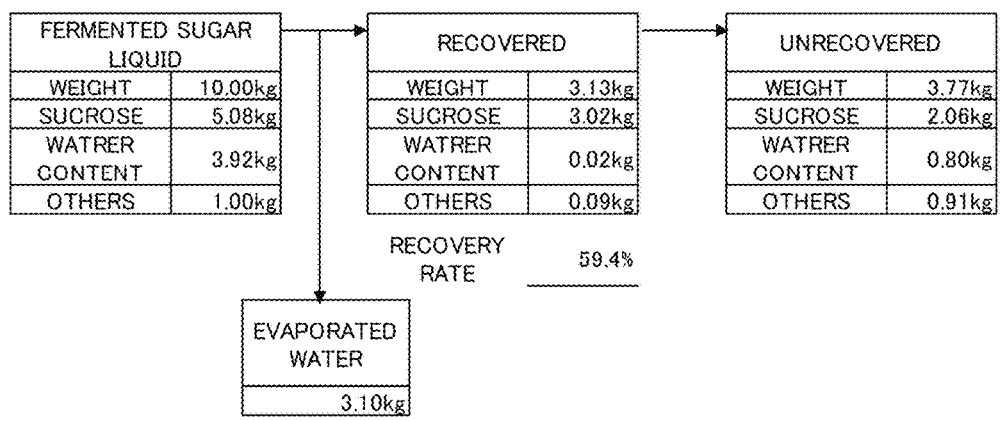
FIG. 8 is a diagram showing material balance in a case where sugar is produced from a raw-material sugar liquid by a method of the present invention.

The sugar liquid obtained by the fermentation test was concentrated under reduced pressure, to obtain a concentrated liquid having Brix of 60%. After the concentrated liquid (Brix 60%, 10 kg) was heated under reduced pressure, 1 kg of sucrose having a particle size of 250 μm was added thereto as seed crystal. The mixture was further heated under reduced pressure, to grow the crystal. A mixture of the crystallized sugar and the sugar liquid was centrifugal machined by a 0.35×4 mm-perforated centrifugal machine at 1,500×g for 5 minutes, to recover sugar. Recovery rate of sucrose was 59.4%. The material balance of this method is shown in FIG. 8.

Figure 9:
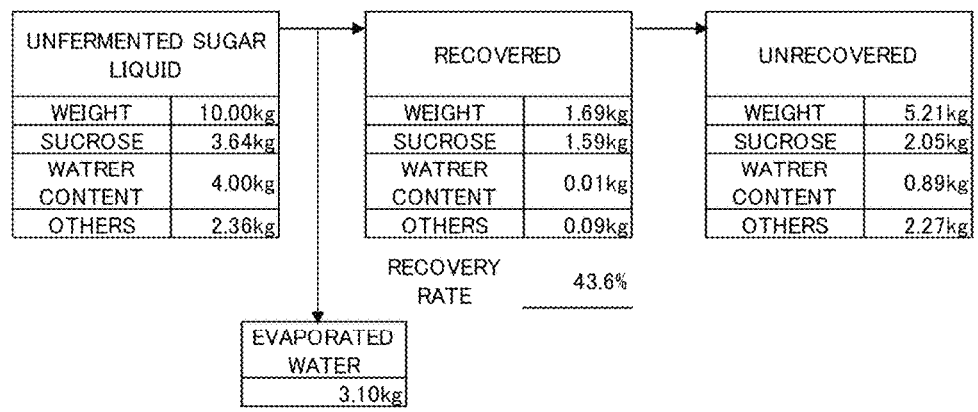
FIG. 9 is a diagram showing material balance in a case where sugar is produced from a raw-material sugar liquid by a conventional method.

As a control, a sugar liquid on which selective fermentation was not carried out (Brix 15%, sucrose 9.9%, glucose 2.7%, fructose 2.8%) was used instead of the clarified fermented liquid, and sucrose was recovered in the same manner. Recovery rate of sucrose was 43.6%. The material balance of this method is shown in FIG. 9.

As shown in the test of sugar production, the selective fermentation of sugar liquid improved recovery efficiency of sucrose.

[Accession Number]

*Saccharomyces cerevisiae* GYK-10 strain was deposited at Incorporated Administrative Agency National Institute of Technology and Evaluation Patent Microorganisms Depositary, located in #122, 2-5-8 Kazusakamatari, Kisarazu-shi, Chiba 292-0818, Japan, on Apr. 11, 2013, and given accession number "NITE BP-1587".

*Saccharomyces cerevisiae* GYK-11 strain was deposited at Incorporated Administrative Agency National Institute of Technology and Evaluation Patent Microorganisms Depositary, located in #122, 2-5-8 Kazusakamatari, Kisarazu-shi, Chiba 292-0818, Japan, on Apr. 11, 2013, and given accession number "NITE BP-1588".

*Saccharomyces cerevisiae* SDT strain was deposited at Incorporated Administrative Agency National Institute of Technology and Evaluation Patent Microorganisms Depositary, located in #122, 2-5-8 Kazusakamatari, Kisarazu-shi, Chiba 292-0818, Japan, on Apr. 11, 2013, and given accession number "NITE BP-1589".

The invention claimed is:

1. *Saccharomyces cerevisiae* strain NITE BP-1587.

2. The *Saccharomyces cerevisiae* strain according to claim 1, wherein the strain is employed for a method of producing sugar and ethanol comprising a step of fermenting sugar liquid derived from a plant with yeast.

3. The *Saccharomyces cerevisiae* strain according to claim 1, wherein the strain is employed for a method of producing sugar and ethanol comprising steps of:
   removing non-sugar components contained in sugar liquid derived from a plant to clarify the sugar liquid; and
   adding yeast to the clarified sugar liquid to carry out ethanol fermentation at a given temperature under an anaerobic condition for an appropriate length of time.

4. A method of producing sugar and ethanol comprising a step of fermenting sugar liquid derived from a plant with the *Saccharomyces cerevisiae* strain according to claim 1.

5. A method of producing sugar and ethanol comprising steps of:
   removing non-sugar components contained in sugar liquid derived from a plant to clarify the sugar liquid; and
   adding the strain according to claim 1 to the clarified sugar liquid to carry out ethanol fermentation at a given temperature under an anaerobic condition for an appropriate length of time.

* * * * *